United States Patent [19]

Kondo et al.

[11] Patent Number: 5,733,477
[45] Date of Patent: Mar. 31, 1998

[54] LIQUID CRYSTAL COMPOSITION AND LIQUID CRYSTAL DISPLAY ELEMENT

[75] Inventors: Tomoyuki Kondo; Yasuhiro Haseba; Yasuyuki Koizumi; Kazutoshi Miyazawa; Norihisa Hachiya; Etsuo Nakagawa, all of Chiba, Japan

[73] Assignee: Chisso Corporation, Osaka, Japan

[21] Appl. No.: 750,326

[22] PCT Filed: Apr. 12, 1996

[86] PCT No.: PCT/JP96/01011

§ 371 Date: Dec. 5, 1996

§ 102(e) Date: Dec. 5, 1996

[87] PCT Pub. No.: WO96/32458

PCT Pub. Date: Oct. 17, 1996

[30] Foreign Application Priority Data

Apr. 12, 1995 [JP] Japan ................................. 7-112551

[51] Int. Cl.[6] .................. C09K 19/20; C09K 19/12; C09K 19/52
[52] U.S. Cl. .................. 252/299.67; 252/299.01; 252/299.63; 252/299.64; 252/299.65; 252/299.66; 428/1
[58] Field of Search .............. 252/299.01, 299.63, 252/299.64, 299.65, 299.66, 299.67; 428/1; 349/182

[56] References Cited

U.S. PATENT DOCUMENTS

| 5,480,581 | 1/1996 | Plach et al. | 252/299.63 |
| 5,487,845 | 1/1996 | Reiffenrath et al. | 252/299.63 |

FOREIGN PATENT DOCUMENTS

| 673986 | 9/1995 | European Pat. Off. . |
| 2-233626 | 9/1990 | Japan . |
| 5-500679 | 2/1993 | Japan . |
| 7-306417 | 11/1995 | Japan . |
| WO 91/15555 | 10/1991 | WIPO . |
| WO 94/03558 | 2/1994 | WIPO . |

*Primary Examiner*—Shean C. Wu
*Attorney, Agent, or Firm*—Wenderoth, Lind & Ponack

[57] ABSTRACT

A liquid crystal composition satisfying various characteristics required for a liquid crystal composition and at the same time having a low temperature threshold voltage, a superior low temperature compatibility and a broad range of nematic phase is provided. A liquid crystal composition characterized by containing as a first component, at least one compound expressed by the following formula (1):

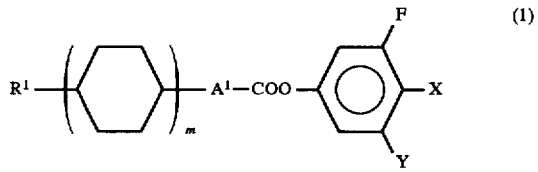

wherein $R^1$ represents an alkyl group of 1 to 10 carbon atoms or an alkenyl group of 2 to 10 carbon atoms; $A^1$ represents trans-1,4-cyclohexylene of 1,4-phenylene wherein one or more hydrogens present on its ring may be replaced by F; X represents $OCF_3$ or $CF_3$; Y represents H or F; and m represents an integer of 0 to 2, and as a second component, at least compound expressed by the following formulas (2-1) to (2-6):

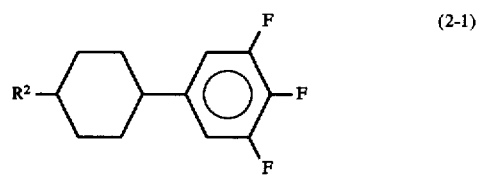

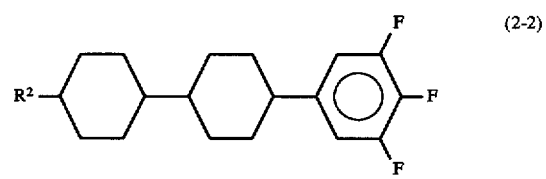

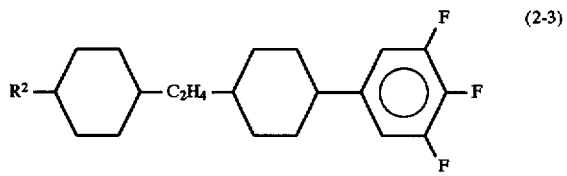

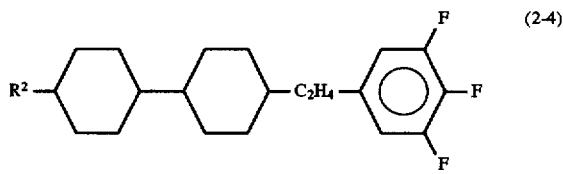

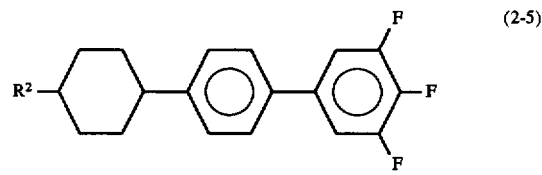

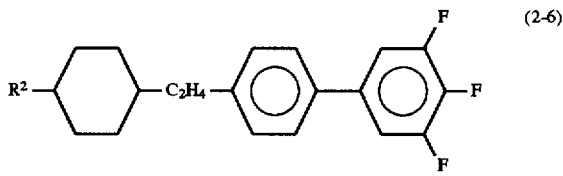

wherein $R^2$ represents an alkyl group of 1 to 10 carbon atoms.

18 Claims, No Drawings

LIQUID CRYSTAL COMPOSITION AND LIQUID CRYSTAL DISPLAY ELEMENT

This application is a 371 of PCT/JP96/01011 filed Apr. 12, 1996.

TECHNICAL FIELD

This invention relates to a novel nematic liquid crystal composition. More particularly, it relates to a liquid crystal composition for an active matrix LCD and a liquid crystal display element constructed using the same.

BACKGROUND OF THE INVENTION

Liquid crystal display element (LCD) has been obtained by filling a liquid crystal composition in a closed cell formed between two sheets of substrates provided with transparent electrodes. This LCD is low in the electric power consumption, small in its size and light in its weight as compared with CRT (Braun tube system display). Thus, LCD has been practically used in terms of various modes such as twisted nematic (TN) mode, supertwisted nematic (STN) mode, thin film transistor (TFT) mode, etc. Among these modes, active matrix LCD (AM-LCD) such as thin film transistor (TFT), etc. has been particularly noted as a prospective winner of flat display in accordance with development of coloring and high precision.

For this AM-LCD liquid crystal composition, the following characteristics have been required:

1) a suitable optical anisotropy ($\Delta n$) in accordance with a cell thickness, 2) a high voltage-holding ratio (VTR) for retaining a high contrast of LCD, 3) a suitable threshold voltage (Vth) in accordance with drive circuit, 4) a wide range of nematic liquid crystal phase (wide range) available in accordance with environment of its use, etc.

Namely, AM-LCD uses a TN display mode wherein the alignment of liquid crystals filled between the upper and lower substrates is twisted by 90° as an operation mode. In this TN display mode, there is a problem of coloring due to interference of liquid crystal cell caused when no voltage is impressed, and in order to prevent this problem and obtain an optimum contrast, it is necessary to set the product of $\Delta n$ by cell thickness d (μm), that is $\Delta n \cdot d$, to a definite value, for example, 0.5 μm. Since there is such a limitation, $\Delta n$ of a liquid crystal composition for TFT currently mainly used, is about 0.07 to 0.11, particularly 0.08 to 0.10 in the 1st. Min. system.

Further, in recent years, as seen from appearance of a small size and lightweight, note type personal computer, development of LCD for portable use, too, has been vigorously carried out. Though such a portable LCD has many restrictions in the aspect of driving electric source, a more lightweight and smaller size and in addition, reduction in the manufacturing cost have been required. As a means for meeting such a requirement, a liquid crystal material having a lower power consumption i.e. a smaller Vth has been devised, and its development has been desired.

Further, along with the above portable use, development of LCD for its outdoor use has come to be studied. In order to endure the outdoor use of the liquid crystal composition, it is necessary to exhibit a nematic phase even in a region exceeding the temperature range under environment of its ordinal use, too. From such a viewpoint, as to liquid crystal compositions for TFT, currently used, those exhibiting 60° C. or higher as upper limit value of a nematic phase transition temperature (clearing point: $T_{NI}$) and $-20°$ C. or lower as lower limit value of the same ($T_L$) have formed a main stream of its use.

In order to meet such a requirement, various liquid crystalline compounds and liquid crystal compositions containing the same have been developed so far. For example, Japanese patent application laid-open No. Hei 2-233626 discloses, in Application example 2, a composition consisting of 15% by weight of a trifluoro compound and 85% by weight of a difluoro compound, each having relatively high dielectric anisotropy value ($\Delta\epsilon$). However, this composition has a drawback that it has a large Vth value; the compatibility of the contained components becomes inferior particularly at low temperatures; and further the range of its nematic phase is narrow.

Further, a publication of WO94/03558 discloses an example of a composition consisting of a trifluoro compound and a difluoro compound. However, those disclosed in Example 1 and Example 2 thereof have a drawback that they have a clearing point as low as 50° C. or lower and a $\Delta n$ as small as 0.06 or less; hence they are deficient in utility. Further, those disclosed in Example 4 and succeeding Examples, have a drawback that the Vth is high.

As described above, liquid crystal compositions have been vigorously researched in accordance with various objects, but the researches have not yet been sufficient; hence it is the present status that novel improvements have been required.

DISCLOSURE OF THE INVENTION

The object of the present invention is to provide a liquid crystal composition having overcome the drawbacks of the above prior art, and satisfying various characteristics sought for AM-LCD liquid crystal composition and particularly having a small Vth, a superior compatibility at low temperatures and a broad range of nematic phase.

The present inventors have made extensive research in compositions using various liquid crystal compounds in order to achieve the above objects, and as a result, have achieved the present invention.

The liquid crystal composition of the present invention comprises, as a first component, at least one member of compounds expressed by the formula (1),

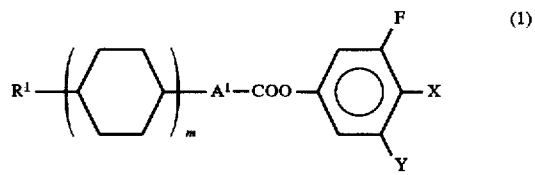

wherein $R^1$ represents an alkyl group of 1 to 10 carbon atoms or an alkenyl group of 2 to 10 carbon atoms; $A^1$ represents trans-1,4-cyclohexylene or 1,4-phenylene which may have one or more Hs replaced by F atom(s) on its ring; X represents $OCF_3$ or $CF_3$; Y represents H or F; and m represents an integer of 0 to 2, and as a second component, at least one member of compounds selected from those of the following formulas (2-1) to (2-6):

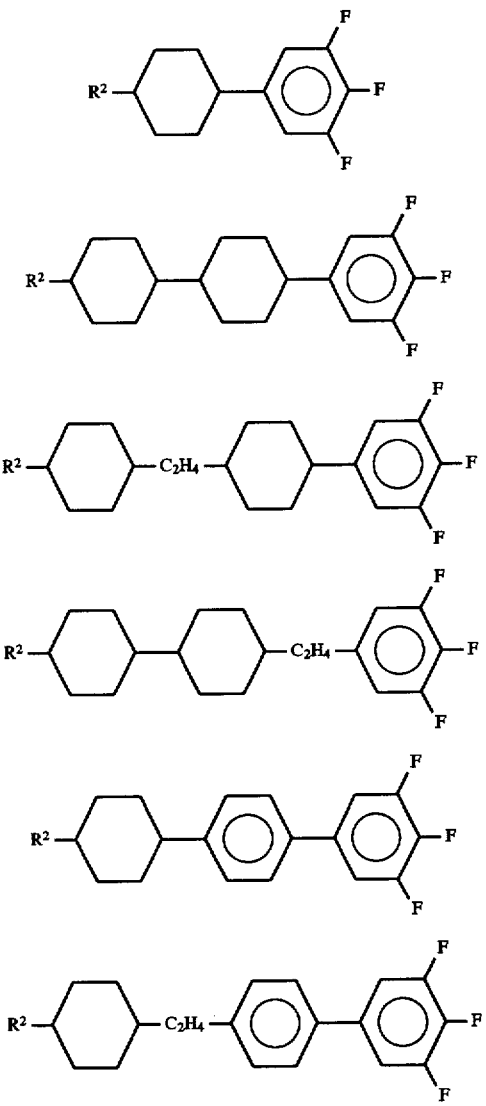

wherein $R^2$ represents an alkyl group of 1 to 10 carbon atoms.

In the above composition of the present invention, it is preferred that the content of the first component is 3 to 50% by weight and that of the second component is 50 to 97% by weight, each based upon the total weight of the liquid crystal composition.

The liquid crystal composition of the present invention may further contain compounds selected from those of a first group expressed by the following formulas (3-1) and/or (3-2), compounds of a second group expressed by the following formulas (4-1) and/or (4-2), and compounds of a third group expressed by the following formulas (5-1) and/or (5-2).

Compounds of a first group:

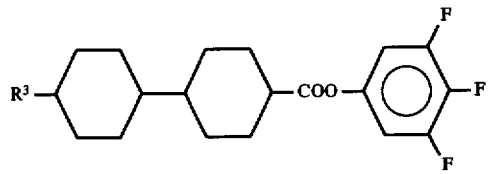

(3-1)

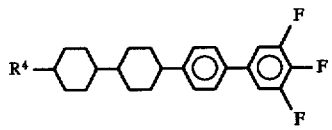

(3-2)

wherein $R^3$ represents an alkyl group of 1 to 10 carbon atoms;

compounds of a second group:

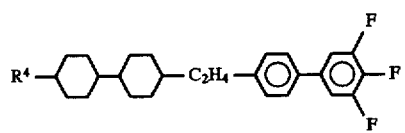

(4-1)

(4-2)

wherein $R^4$ represents an alkyl group of 1 to 10 carbon atoms;

compounds of a third group:

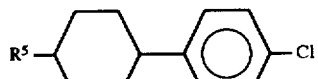

(5-1)

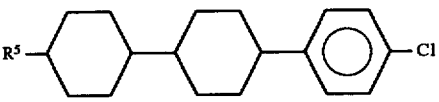

(5-2)

wherein $R^5$ represents an alkyl group of 1 to 10 carbon atoms.

By using these liquid crystal compounds of the present invention, it is possible to obtain a liquid crystal display element satisfying the object of the present invention.

BEST MODE FOR PRACTICING THE PRESENT INVENTION

The first component used in the liquid crystal composition of the present invention is one or more compounds expressed by the formula (1), but as more concrete and preferred examples, compounds expressed by the following formulas (1-1) to (1-16) can be mentioned:

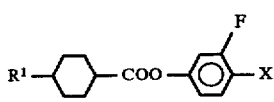

(1-1)

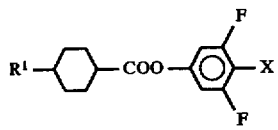

(1-2)

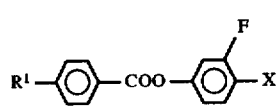

(1-3)

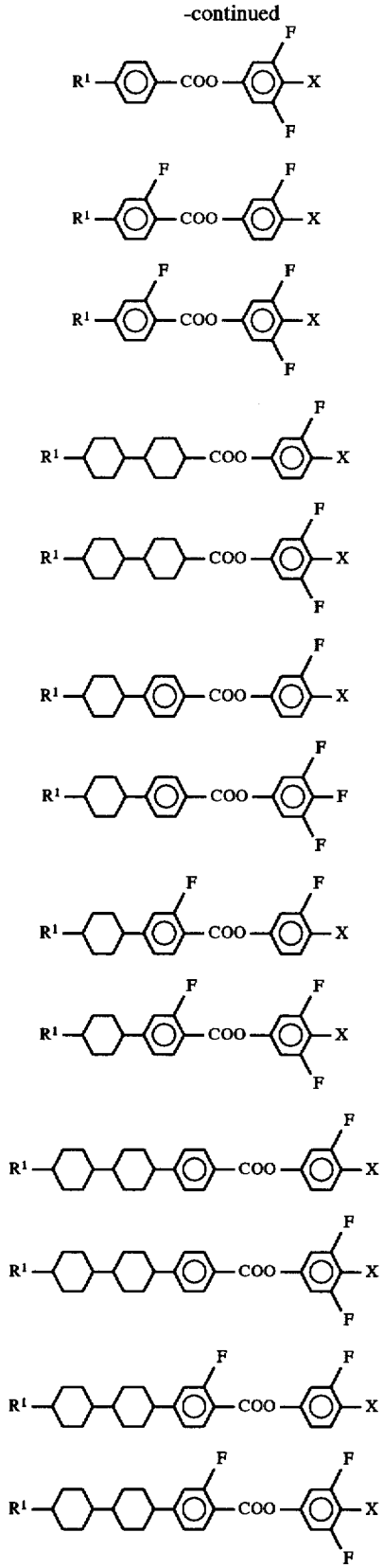

In these formulas, $R^1$ and X are as described above.

Among the above compounds, compounds expressed by the formulas (1-4), (1-7), (1-8), (1-9) (1-10) and (1-16) are preferably used.

Compounds of the first component generally have a $\Delta\epsilon$ value in the range of 10 to 40 and further are excellent in the thermal stability and the chemical stability; hence particularly they have a role of reducing the Vth value of the liquid crystal composition for TFT.

The content of the first component is preferably 3 to 50% by weight, more preferably 3 to 20% by weight, based upon the total weight of the liquid crystal composition. On the contrary, if the content is lower than 3% by weight, it is difficult to obtain the effectiveness of a low Vth among the objects of the present invention; and if the content exceeds 50% by weight, there may be a case where the low temperature compatibility of the liquid crystal composition becomes inferior.

The compounds expressed by the formulas (2-1) to (2-6) of the second component are trifluoro compounds as well as the compounds of the above first group and second group, and as apparent from the above Japanese patent application laid-open No. Hei 2-233626, the compounds have a $\Delta\epsilon$ in the range of about 7 to 12, and have a superior thermal stability and chemical stability; hence they have been known as compounds for low voltage TFT (R. Tarao et al., SID 94 Digest, p.233).

Among the compounds of the second component, those expressed by the formula (2-1) of a bicyclic structure have a particular role of reducing the Vth of the liquid crystal composition, but use of a large quantity thereof may reduce the clearing point ($T_{NI}$) of the liquid crystal composition; hence it is necessary to take care.

The compounds expressed by the formulas (2-2) to (2-6) of the tricyclic structure have a $T_{NI}$ in the range of about 50° to 100° C.; hence they are most suitable as a base compound of compositions for low voltage TFT.

The content of the second component is preferably 50 to 97% by weight based upon the total weight of the liquid crystal composition, more preferably 60 to 95% by weight. If the content is lower than 50% by weight, the compatibility of the liquid crystal composition may become inferior particularly at low temperatures. On the contrary, if the content exceeds 97% by weight, it is difficult to obtain the low voltage effectiveness as one of the objects of the present invention.

Among the compounds of the first group to the third group, which may be further added to the liquid crystal composition of the present invention, the compounds expressed by the formulas (3-1) and (3-2) of the first group, are trifluoro compounds of ester group and have a role of particularly reducing the Vth value of liquid crystal compositions, but use of a large quantity thereof may deteriorate the low temperature compatibility of the liquid crystal composition.

Accordingly, the content is preferably 30% by weight or lower, based upon the total weight of the liquid crystal composition, more preferably 20% by weight or lower.

Next, compounds expressed by the formulas (4-1) and (4-2) of the second group are tetracyclic trifluoro compounds, and have a role of particularly elevating the $T_{NI}$ value of the liquid crystal composition.

However, since they are tetracyclic compounds, use of a large quantity thereof may elevate the Vth value of the liquid crystal composition or deteriorate the low temperature compatibility. Thus, the content is preferably 20% by weight or less, based upon the total weight of the liquid crystal composition, more preferably 10% by weight or lower.

Compounds expressed by the formulas (5-1) and (5-2) of the third group are bicyclic or tricyclic chloro (Cl) group compounds and have a role of mainly lowering the viscosity of the liquid crystal composition.

Since these compounds have a small Δε of 4 to 5, use of a large quantity thereof may elevate the Vth of the liquid crystal composition. Thus, the content is preferably 20% by weight or lower based upon the total weight of the liquid crystal composition, more preferably 15% by weight or lower.

The composition of the present invention may further contain another compound in addition to the above compounds of the first group to the third group, in order to improve the objectives of the present invention, for example, Vth, low temperature compatibility, nematic phase range, etc.

The liquid crystal composition can be prepared according to processes which are conventional by themselves, for example, a process which dissolves various components with each other at high temperatures, a process which dissolves the respective components in an organic solvent and mixes them, followed by distilling off the solvent under reduced pressure, etc.

Further, if necessary, by adding suitable additives, improvement in accordance with objective uses is made, whereby the liquid crystal composition is optimized. Such additives have been known by persons skilled in the art, and have been described in detail. Usually, in order to induce the helical structure of liquid crystals, adjust necessary twist angle and prevent reverse twist, chiral dopants or the like are added.

Further, when a dichroic pigment such as those of mellocyanine group, styryl group, azo group, azomethine group, azoxy group, quinophthalone group, anthraquinone group, tetrazine group, etc. is added, the resulting liquid crystal composition can be also used as a liquid crystal composition for guest-host (GH) mode.

The liquid crystal composition of the present invention can be also used for a polymer dispersion type liquid crystal display element (PDLCD) represented by NCAP prepared by microcapsulating nematic liquid crystals or polymer network liquid crystal display element obtained by forming three-dimensional, reticular high polymer in liquid crystals (PNLCD) and besides, can be also used as liquid crystal compositions for birefringence control (ECB) mode or dynamic scattering (DS) mode.

The present invention will be described in detail by way of Examples, but it should not be construed to be limited thereto.

In addition, in the compositions mentioned in Examples and Comparative examples, designations of compounds are defined in the following Table 1. In this Table, left terminal groups are abbreviated to n-, nO-, nOm-, V-, Vn-, nVm- and nVmVk- (n, m and k mean an integer of 1 or more); bonding groups are abbreviated to 2, 4, E, T, V, CF2O and OCF2; ring structures are abbreviated to B, B(F), B(F,F), H, Py, D and Ch; and right terminal groups are abbreviated to -F, -CL, -CF3, -OCF3, -OCF2H, -n, -On, -Eme, -nV and -mVn (n and m are an integer of 1 or more). The contents of the respective components mean % by weight, unless otherwise indicated.

Further, the characteristic data of the liquid crystal compositions are abbreviated as follows:

$T_{NI}$ (clearing point), $T_L$ (lower limit value of nematic phase transition points), $\eta_{20}$ (viscosity at 20° C.), Δn (optical anisotropy at 25° C.), Δε (dielectric anisotropy at 25° C.), Vth (threshold voltage at 25° C.), and VHR (voltage-holding ratio sought based upon area method). As to the above $T_L$, the composition was allowed to stand in the respective freezers at 0° C., -10° C., -20° C. and -30° C., for 30 days followed by judging it based upon the resulting liquid crystal phases.

TABLE 1

| Left terminal group | Symbol |
|---|---|
| $C_nH_{2n+1}-$ | n- |
| $C_nH_{2n+1}O-$ | nO- |
| $C_nH_{2n+1}OC_mH_{2m}-$ | nOm- |
| $CH_2=CH-$ | V- |
| $CH_2=CHC_nH_{2n}-$ | Vn- |
| $C_nH_{2n+1}CH=CHC_mH_{2m}-$ | nVm- |
| $C_nH_{2n+1}CH=CHC_mH_{2m}CH=CHC_kH_{2k}-$ | nVmVk- |

| Bonding group | Symbol |
|---|---|
| $-C_2H_4-$ | 2 |
| $-C_4H_8-$ | 4 |
| $-COO-$ | E |
| $-C\equiv C-$ | T |
| $-CH=CH-$ | V |
| $-CF_2O-$ | CF2O |
| $-OCF_2-$ | OCF2 |

| Ring structure | Symbol |
|---|---|
| 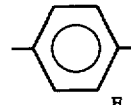 | B |
| 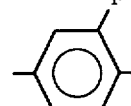 | B(F) |
| 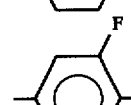 | B(F,F) |
| 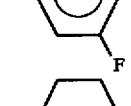 | H |
| 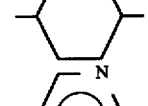 | Py |
| 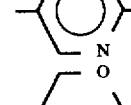 | D |
| 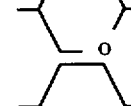 | Ch |

| Right terminal group | Symbol |
|---|---|
| -F | -F |
| -Cl | -CL |
| -CN | -C |
| -CF3 | -CF3 |
| -OCF3 | -OCF3 |
| -OCF2H | -OCF2H |
| $-C_nH_{2n+1}$ | -n |
| $-OC_nH_{2n+1}$ | -On |
| -COOCH3 | -EMe |
| $-C_nH_{2n}CH=CH_2$ | -nV |
| $-C_mH_{2m}CH=CHC_nH_{2n+1}$ | -mVn |

COMPARATIVE EXAMPLE 1

The above application example 2 of Japanese patent application laid-open No. Hei 2-233626 discloses the following composition:

| | |
|---|---|
| 3-HHB(F,F)-F | 15.0% |
| 2-HHB(F)-F | 28.4% |
| 3-HHB(F)-F | 28.3% |
| 5-HHB(F)-F | 28.3% |

The characteristics of this composition were sought, and they were as follows:

$T_{NI}$=110.7° C.
$T_L$<0° C.
$\eta_{20}$=25.0 mPa.s
$\Delta n$=0.077
Vth=2.32 (V)
VHR=98.8%

As apparent from the above results, it is known that this liquid crystal composition has a large Vth value and further an inferior low temperature compatibility (a high $T_L$).

COMPARATIVE EXAMPLE 2

Example 1 of the above publication WO94/03558 discloses the following composition:

| | |
|---|---|
| 7-HB(F,F)-F | 10.0% |
| 2-HHB(F,F)-F | 25.0% |
| 3-HHB(F,F)-F | 35.0% |
| 5-HHB(F,F)-F | 18.0% |
| 7-HB(F)-F | 12.0% |

The characteristics of this composition were sought, and they were as follows:

$T_{NI}$=42.9° C.
$T_L$<0° C.
$\eta_{20}$=22.2 mPa.s
$\Delta n$=0.059
Vth=1.07 (V)
VHR=98.7%

As apparent from the above results, it is known that this liquid crystal composition has a small Vth but a low $T_{NI}$, and an inferior low temperature compatibility (high $T_L$) and further a small $\Delta n$ value; hence it is deficient in the utility.

COMPARATIVE EXAMPLE 3

In Example 2 of the above publication WO94/03558 shown in the above comparative example 2, the following composition is disclosed:

| | |
|---|---|
| 2-HHB(F,F)-F | 26.0% |
| 3-HHB(F,F)-F | 26.0% |
| 5-HHB(F,F)-F | 26.0% |
| 7-HB(F)-F | 12.0% |
| 5-H2B(F)-F | 10.0% |

The characteristics of this composition were sought, and they were as follows:

$T_{NI}$=46.0° C.
$T_L$<0° C.
$\eta_{20}$=21.6 mPa.s
$\Delta n$=0.058
Vth=1.17 (V)
VHR=98.5%

As apparent from the above results, it is known that this liquid crystal composition has a small Vth but a low $T_{NI}$, and an inferior low temperature compatibility (high $T_L$) and a small $\Delta n$ value; hence it is deficient in the utility.

COMPARATIVE EXAMPLE 4

Example 4 of the above publication WO94/03558 discloses the following composition:

| | |
|---|---|
| 2-HHB(F,F)-F | 10.0% |
| 3-HHB(F,F)-F | 10.0% |
| 5-HHB(F,F)-F | 10.0% |
| 5-H2B(F)-F | 10.0% |
| 5-HEB-F | 7.5% |
| 7-HEB-F | 7.5% |
| 2-HHB(F)-F | 11.7% |
| 3-HHB(F)-F | 11.7% |
| 5-HHB(F)-F | 11.6% |
| 3-HHB-F | 5.0% |
| 5-HHEB-F | 2.5% |
| 7-HHEB-F | 2.5% |

The characteristics of this composition were sought, and they were as follows:

$T_{NI}$=71.3° C.
$T_L$<-20° C.
$\eta_{20}$=19.2 mPa.s
$\Delta n$=0.070
Vth=1.77 V
VHR=98.2%

As apparent from the above results, it is known that this liquid crystal composition has a comparatively high clearing point of about 70° C. and nevertheless a large Vth, and a somewhat small $\Delta n$ value.

EXAMPLE 1

A liquid crystal composition consisting of the following compounds and contents was prepared:

| | |
|---|---|
| 1V2-BEB(F,F)-CF3 | 4.0% |
| 5-HHEB(F,F)-CF3 | 5.0% |
| 3-HBEB(F,F)-CF3 | 3.0% |
| 3-HHB(F)EB(F,F)-CF3 | 3.0% |
| 3-H2HB(F,F)-F | 10.0% |
| 4-H2HB(F,F)-F | 8.0% |
| 5-H2HB(F,F)-F | 10.0% |
| 3-HHB(F,F)-F | 10.0% |
| 3-HH2B(F,F)-F | 15.0% |
| 5-HH2B(F,F)-F | 10.0% |
| 3-HBB(F,F)-F | 10.0% |
| 5-HBB(F,F)-F | 12.0% |

The characteristics of this composition were sought and they were as follows:

$T_{NI}$=80.4° C.
$T_L$<-30° C.
$\eta_{20}$=29.3 mPa.s
$\Delta n$=0.091
$\Delta\epsilon$=11.7
Vth=1.28 V
VHR=98.6%

This liquid crystal composition has a superior low temperature compatibility as compared with those of Comparative examples 1 to 4. Further, its nematic phase temperature range is wide to an extent which raises no practical problem (that is, a high $T_{NI}$), and still further, Vth exhibits a small value as well, and in a collective view, it is well balanced and abundant in utility.

EXAMPLE 2

A liquid crystal composition consisting of the following compounds and contents was prepared:

| | |
|---|---|
| 5-HHEB(F)-OCF3 | 3.0% |
| 2-HBEB(F)-OCF3 | 2.0% |
| 3-H2HB(F,F)-F | 12.0% |
| 4-H2HB(F,F)-F | 10.0% |
| 5-H2HB(F,F)-F | 10.0% |
| 3-HHB(F,F)-F | 10.0% |
| 4-HHB(F,F)-F | 4.0% |
| 3-HH2B(F,F)-F | 10.0% |
| 5-HH2B(F,F)-F | 13.0% |
| 3-HBB(F,F)-F | 13.0% |
| 5-HBB(F,F)-F | 13.0% |

The characteristics of this composition were sought and they were as follows:

$T_{NI}$=80.3° C.

$T_L$<-30° C.

$\eta_{20}$=28.3 mPa.s $\Delta n$=0.089

$\Delta \epsilon$=8.7

Vth=1.55 V

VHR=98.7%

EXAMPLE 3

A liquid crystal composition consisting of the following compounds and contents was prepared:

| | |
|---|---|
| 5-HHEB(F,F)-CF3 | 6.0% |
| 3-HBEB(F,F)-CF3 | 3.0% |
| 3-HHB(F)EB(F,F)-CF3 | 3.0% |
| 7-HB(F,F)-F | 3.0% |
| 3-H2HB(F,F)-F | 12.0% |
| 4-H2HB(F,F)-F | 8.0% |
| 5-H2HB(F,F)-F | 10.0% |
| 3-HHB(F,F)-F | 10.0% |
| 3-HH2B(F,F)-F | 15.0% |
| 5-HH2B(F,F)-F | 10.0% |
| 3-HBB(F,F)-F | 8.0% |
| 5-HBB(F,F)-F | 12.0% |

The characteristics of this composition were sought and they were as follows:

$T_{NI}$=81.2° C.

$T_L$<-30° C.

$\eta_{20}$=28.5 mPa.s $\Delta n$=0.087

$\Delta \epsilon$=10.4

Vth=1.36 V

VHR=98.6%

EXAMPLE 4

A liquid crystal composition consisting of the following compounds and contents was prepared:

| | |
|---|---|
| 1V2-BEB(F,F)-CF3 | 3.0% |
| 5-HHEB(F,F)-CF3 | 7.0% |
| 7-HB(F,F)-F | 6.0% |
| 3-HBB(F,F)-F | 9.0% |
| 5-HBB(F,F)-F | 4.0% |
| 5-H2BB(F,F)-F | 4.0% |
| 3-HHB(F,F)-F | 7.0% |
| 3-HH2B(F,F)-F | 10.0% |
| 5-HH2B(F,F)-F | 5.0% |
| 3-H2HB(F,F)-F | 9.0% |
| 4-H2HB(F,F)-F | 8.0% |
| 5-H2HB(F,F)-F | 8.0% |
| 3-HHEB(F,F)-F | 10.0% |
| 5-HHEB(F,F)-F | 4.0% |
| 2-HBEB(F,F)-F | 3.0% |
| 5-HBEB(F,F)-F | 3.0% |

The characteristics of this composition were sought and they were as follows:

$T_{NI}$=70.3° C.

$T_L$<-30° C.

$\eta_{20}$=28.5 mPa.s $\Delta n$=0.084

$\Delta \epsilon$=11.2

Vth=1.33 V

VHR=98.4%

EXAMPLE 5

A liquid crystal composition consisting of the following compounds was prepared:

| | |
|---|---|
| 5-HHEB(F)-OCF3 | 5.0% |
| 5-HHEB(F,F)-CF3 | 5.0% |
| 3-H2HB(F,F)-F | 7.0% |
| 4-H2HB(F,F)-F | 7.0% |
| 5-H2HB(F,F)-F | 6.0% |
| 3-HH2B(F,F)-F | 6.0% |
| 3-HBB(F,F)-F | 28.0% |
| 5-HBB(F,F)-F | 26.0% |
| 3-HHEB(F,F)-F | 10.0% |

The characteristics of this composition were sought and they were as follows:

$T_{NI}$=70.0° C.

$T_L$<-30° C.

$\eta_{20}$=33.6 mPa.s $\Delta n$=0.100

$\Delta \epsilon$=10.2

Vth=1.33 V

VHR=98.6%

EXAMPLE 6

A liquid crystal composition consisting of the following compounds and contents was prepared:

| | |
|---|---|
| 1V2-BEB(F,F)-CF3 | 3.0% |
| 3-H2HB(F,F)-F | 9.0% |
| 4-H2HB(F,F)-F | 9.0% |
| 5-H2HB(F,F)-F | 9.0% |
| 3-HBB(F,F)-F | 30.0% |
| 5-HBB(F,F)-F | 30.0% |
| 3-HHBB(F,F)-F | 6.0% |
| 5-HHBB(F,F)-F | 4.0% |

The characteristics of this composition were sought and they were as follows:

$T_{NI}=71.6°$ C.
$T_L<-30°$ C.
$\eta_{20}=34.3$ mPa.s
$\Delta n=0.112$
$\Delta\epsilon=10.4$
Vth=1.37 V
VHR=98.8%

EXAMPLE 7

A liquid crystal composition consisting of the following compounds and contents was prepared:

| | |
|---|---|
| 3-HBEB(F,F)-CF3 | 3.0% |
| 5-HHEB(F,F)-CF3 | 5.0% |
| 7-HB(F,F)-F | 10.0% |
| 3-H2HB(F,F)-F | 10.0% |
| 4-H2HB(F,F)-F | 10.0% |
| 5-H2HB(F,F)-F | 10.0% |
| 3-HHB(F,F)-F | 10.0% |
| 4-HHB(F,F)-F | 5.0% |
| 3-HH2B(F,F)-F | 10.0&  |
| 3-HBB(F,F)-F | 10.0% |
| 5-HBB(F,F)-F | 7.0% |
| 3-HHBB(F,F)-F | 5.0% |
| 3-HH2BB(F,F)-F | 5.0% |

The characteristics of this composition were sought and they were as follows:
$T_{NI}=77.2°$ C.
$T_L<-30°$ C.
$\eta_{20}=28.1$ mPa.s
$\Delta n=0.087$
$\Delta\epsilon=9.5$
Vth=1.50 V
VHR=98.6%

EXAMPLE 8

A liquid crystal composition consisting of the following compounds and contents was prepared:

| | |
|---|---|
| 1V2-BEB(F,F)-CF3 | 4.0% |
| 3-H2HB(F,F)-F | 12.0% |
| 4-H2HB (F,F) -F | 10.0% |
| 5-H2HB(F,F)-F | 10.0% |
| 3-HHB(F,F)-F | 5.0% |
| 3-HH2B (F,F9-F | 10.0% |
| 5-HH2B(F,F)-F | 10.0% |
| 3-HBB(F,F)-F | 12.0% |
| 5-HBB(F,F)-F | 12.0 |
| 5-HB-CL | 5.0% |

The characteristics of this composition were sought and they were as follows:
$T_{NI}=70.4°$ C.
$T_L<-30°$ C.
$\eta_{20}=27.0$ mPa.s
$\Delta n=0.089$
$\Delta\epsilon=9.9$
Vth=1.47 V
VHR=98.8%

EXAMPLE 9

A liquid crystal composition consisting of the following compounds and contents was prepared:

| | |
|---|---|
| 5-HHEB(F)-OCF3 | 4.0% |
| 3-HBEB(F,F)-CF3 | 5.0% |
| 3-H2BB(F,F)-F | 5.0% |
| 5-H2BB(F,F)-F | 5.0% |
| 3-H2HB(F,F)-F | 7.0% |
| 4-H2HB(F,F)-F | 7.0% |
| 5-H2HB(F,F)-F | 7.0% |
| 3-HH2B(F,F)-F | 9.0% |
| 5-HH2B(F,F)-F | 9.0% |
| 5-HBB(F,F)-F | 25.0% |
| 5-HB-CL | 5.0% |
| 5-HHB-CL | 3.0% |
| 2-HHBB(F,F)-F | 4.0% |
| 5-HHBB(F,F)-F | 5.0% |

The characteristics of this composition were sought and they were as follows:
$T_{NI}=88.5°$ C.
$T_L<-30°$ C.
$\eta_{20}=29.7$ mPa.s
$\Delta n=0.103$
$\Delta\epsilon=10.0$
Vth=1.54 V
VHR=98.8%

EXAMPLE 10

A liquid crystal composition consisting of the following compounds and contents was prepared:

| | |
|---|---|
| 1V2-BEB(F,F)-CF3 | 5.0% |
| 2-HBEB(F,F)-OCF3 | 3.0% |
| 7-HB(F,F)-F | 5.0% |
| 3-HBB(F,F)-F | 9.0% |
| 3-HH2B(F,F)-F | 11.0% |
| 5-HH2B(F,F)-F | 10.0% |
| 3-H2HB(F,F)-F | 10.0% |
| 4-H2HB(F,F)-F | 10.0% |
| 5-H2HB(F,F)-F | 10.0% |
| 3-HHEB(F,F)-F | 8.0% |
| 2-HBEB(F,F)-F | 3.0% |
| 5-HBEB(F,F)-F | 3.0% |
| 5-HB-CL | 3.0% |
| 2-HHBB(F,F)-F | 5.0% |
| 3-HHBB(F,F)-F | 5.0% |

The characteristics of this composition were sought and they were as follows:
$T_{NI}=80.5°$ C.
$T_L<-30°$ C.
$\eta_{20}=30.5$ mPa.s
$\Delta n=0.091$
$\Delta\epsilon=12.0$
Vth=1.29 V
VHR=98.5%

EXAMPLE 11

A liquid crystal composition consisting of the following compounds and contents was prepared:

| | |
|---|---|
| 5-HHEB(F,F)-OCF3 | 5.0% |
| 7-HB(F,F)-F | 10.0% |
| 3-HBB(F,F)-F | 15.0% |
| 3-HH2B(F,F)-F | 9.0% |
| 5-HH2B(F,F)-F | 6.0% |

-continued

| | |
|---|---|
| 3-H2HB(F,F)-F | 10.0% |
| 4-H2HB(F,F)-F | 10.0% |
| 5-H2HB(F,F)-F | 10.0% |
| 3-HHEB(F,F)-F | 9.0% |
| 2-HBEB(F,F)-F | 3.0% |
| 5-HBEB(F,F)-F | 3.0% |
| 2-HHBB(F,F)-F | 5.0% |
| 3-HHBB(F,F)-F | 5.0% |

The characteristics of this composition were sought and they were as follows:

$T_{NI}$=79.8° C.

$T_L$<−30° C.

$\eta_{20}$=31.2 mPa.s $\Delta n$=0.087

$\Delta\epsilon$=10.6

Vth=1.35 V

VHR=98.5%

COMMERCIAL UTILIZABILITY

As described above, according to the present invention, it is possible to provide a liquid crystal composition which satisfies various characteristics required for a liquid crystal composition for AM-LCD, and at the same time, has particularly a small Vth, and a superior low temperature compatibility and a broad range of nematic phase range.

We claim:

1. A liquid crystal composition comprising, as a first component, at least one compound expressed by the formula (1),

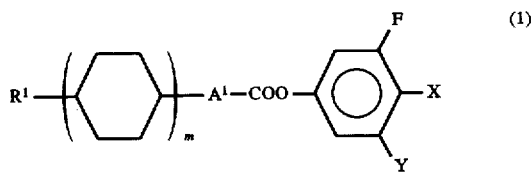

wherein $R^1$ represents an alkyl group of 1 to 10 carbon atoms or an alkenyl group of 2 to 10 carbon atoms; $A^1$ represents trans-1,4-cyclohexylene or 1,4-phenylene which may have one or more hydrogens replaced by F atom(s) on its ring; X represents $OCF_3$ or $CF_3$; Y represents H or F; and m represents an integer of 0 to 2, and as a second component, at least one compound selected from those of the following formulas (2-1) to (2-6):

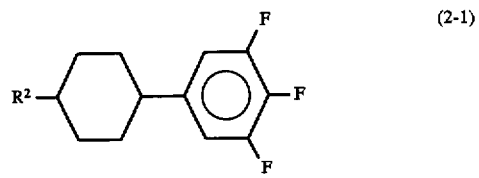

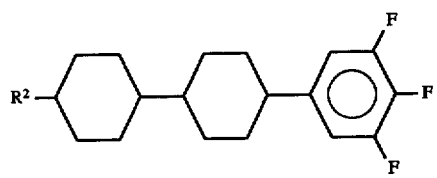

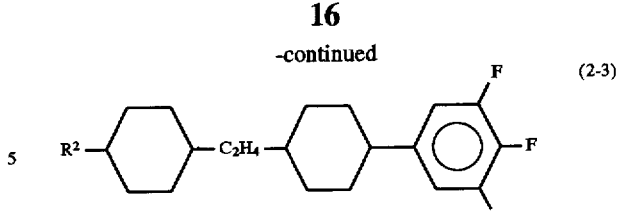

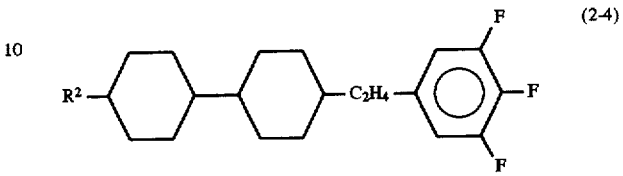

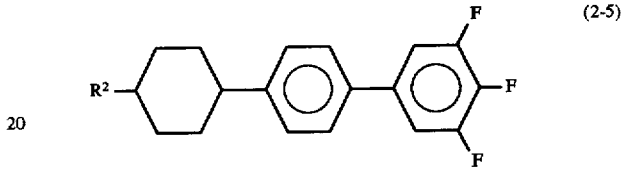

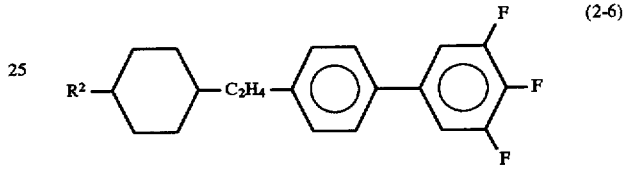

wherein $R^2$ represents an alkyl group of 1 to 10 carbon atoms.

2. A liquid crystal composition according to claim 1, wherein the contents of said first component and said second component are respectively 3 to 50% by weight and 50 to 97% by weight, each based upon the total weight of the liquid crystal composition.

3. A liquid crystal composition according to claim 1 or claim 2, which further contains compounds expressed by the following formulas (3-1) and/or (3-2):

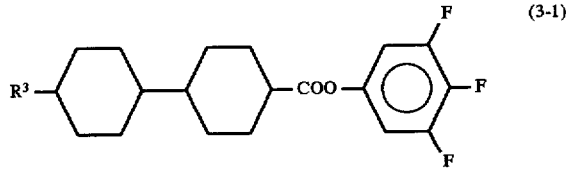

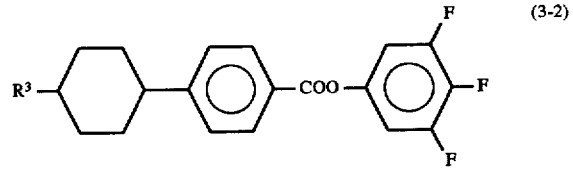

wherein $R^3$ represents an alkyl group of 1 to 10 carbon atoms.

4. A liquid crystal composition according to claim 1 or claim 2, which further contains compounds expressed by the following formulas (4-1) and/or (4-2):

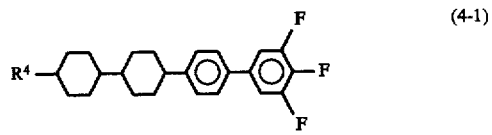

-continued

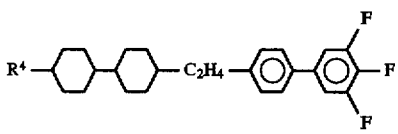
(4-2)

wherein R⁴ represents an alkyl group of 1 to 10 carbon atoms.

5. A liquid crystal composition according to claim 1 or claim 2, which further contains compounds expressed by the following formulas (5-1) and/or (5-2):

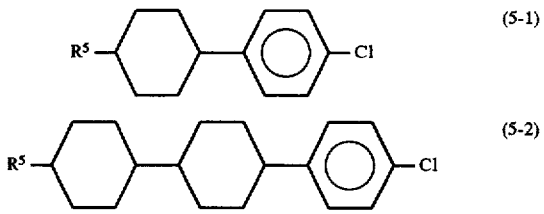

wherein R⁵ represents an alkyl group of 1 to 10 carbon atoms.

6. A liquid crystal display element comprising a liquid crystal composition according to claim 1.

7. A liquid crystal display element comprising a liquid crystal composition according to claim 2.

8. A liquid crystal display element comprising a liquid crystal composition according to claim 3.

9. A liquid crystal display element comprising a liquid crystal composition according to claim 4.

10. A liquid crystal display element comprising a liquid crystal composition according to claim 5.

11. A liquid crystal composition according to claim 3, which further contains compounds expressed by the following formulas (4-1) and/or (4-2):

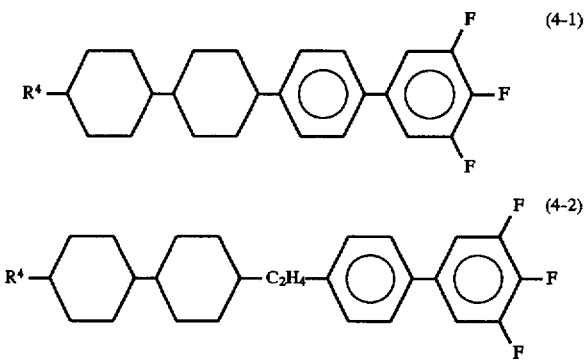

wherein R⁴ represents an alkyl group of 1 to 10 carbon atoms.

12. A liquid crystal composition according to claim 3, which further contains compounds expressed by the following formulas (5-1) and/or (5-2):

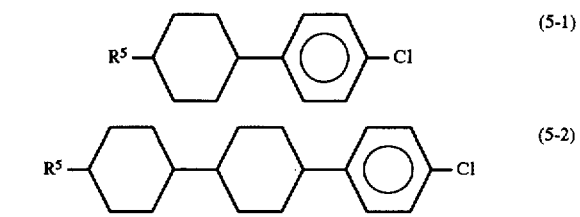

wherein R⁵ represents an alkyl group of 1 to 10 carbon atoms.

13. A liquid crystal composition according to claim 4, which further contains compounds expressed by the following formulas (5-1) and/or (5-2):

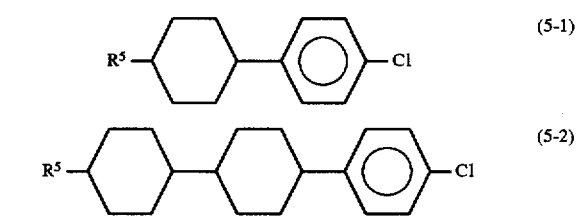

wherein R⁵ represents an alkyl group of 1 to 10 carbon atoms.

14. A liquid crystal composition according to claim 11, which further contains compounds expressed by the following formulas (5-1) and/or (5-2):

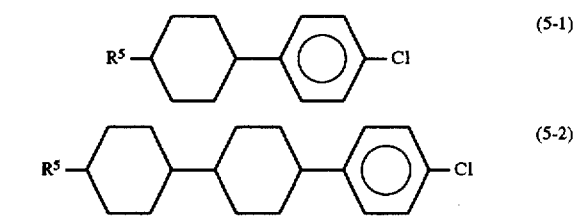

wherein R⁵ represents an alkyl group of 1 to 10 carbon atoms.

15. A liquid crystal display element comprising a liquid crystal composition according to claim 11.

16. A liquid crystal display element comprising a liquid crystal composition according to claim 12.

17. A liquid crystal display element comprising a liquid crystal composition according to claim 13.

18. A liquid crystal display element comprising a liquid crystal composition according to claim 14.

* * * * *